United States Patent
Mancini et al.

(10) Patent No.: US 12,377,035 B2
(45) Date of Patent: Aug. 5, 2025

(54) PEPTIDES FOR INHIBITING CHOLINERGIC CALCITONIN GENE-RELATED PEPTIDE (CGRP) AND ACETYLCHOLINE (ACH) RELEASE OR INHIBITING SENSITIZATION-MEDIATED BY TRPV1-MEDIATED EXCITABILITY IN SENSORY NEURONS AND METHODS OF USE THEREOF

(71) Applicant: AZIENDE CHIMICHE RIUNITE ANGELINI FRANCESCO—A.C.R.A.F. S.p.A., Rome (IT)

(72) Inventors: Francesca Mancini, Nettuno (IT); Isabel Devesa Giner, Elche (ES); Antonio Ferrer Montiel, Alicante (ES); Gregorio Fernandez Ballester, Murcia (ES); Giorgina Mangano, Rome (IT); Cristina Bartella, Rome (IT)

(73) Assignee: AZIENDE CHIMICHE RIUNITE ANGELINI FRANCESCO—A.C.R.A.F. S.p.A., Rome (IT)

( * ) Notice: Subject to any disclaimer, the term of this patent is extended or adjusted under 35 U.S.C. 154(b) by 945 days.

(21) Appl. No.: 15/734,125

(22) PCT Filed: Jun. 11, 2019

(86) PCT No.: PCT/EP2019/065219
§ 371 (c)(1),
(2) Date: Dec. 1, 2020

(87) PCT Pub. No.: WO2019/238683
PCT Pub. Date: Dec. 19, 2019

(65) Prior Publication Data
US 2022/0296489 A1    Sep. 22, 2022

(30) Foreign Application Priority Data
Jun. 13, 2018 (EP) .................................... 18177586

(51) Int. Cl.
| | | |
|---|---|---|
| C07K 4/00 | (2006.01) |
| A61K 8/64 | (2006.01) |
| A61K 38/00 | (2006.01) |
| A61K 38/04 | (2006.01) |
| A61K 38/08 | (2019.01) |
| A61K 38/10 | (2006.01) |
| A61P 25/00 | (2006.01) |
| A61P 25/02 | (2006.01) |
| A61P 25/04 | (2006.01) |
| A61P 27/00 | (2006.01) |
| A61P 29/02 | (2006.01) |
| A61Q 19/08 | (2006.01) |
| C07K 7/00 | (2006.01) |
| C07K 7/06 | (2006.01) |
| C07K 7/08 | (2006.01) |

(52) U.S. Cl.
CPC ................ *A61K 8/64* (2013.01); *A61K 38/04* (2013.01); *A61K 38/08* (2013.01); *A61K 38/10* (2013.01); *A61P 25/00* (2018.01); *A61P 25/02* (2018.01); *A61P 25/04* (2018.01); *A61P 27/00* (2018.01); *A61P 29/02* (2018.01); *A61Q 19/08* (2013.01); *C07K 7/06* (2013.01); *C07K 7/08* (2013.01); *A61K 38/00* (2013.01)

(58) Field of Classification Search
CPC .... A61K 38/04; C07K 14/57527; C07K 7/06; C07K 7/08; A61P 25/00; A61P 37/08
See application file for complete search history.

(56) References Cited

U.S. PATENT DOCUMENTS

| | | | | |
|---|---|---|---|---|
| 10,466,250 B2 * | 11/2019 | Alving | ............... | G01N 33/6848 |
| 11,215,615 B2 * | 1/2022 | Getts | .................... | G01N 33/564 |
| 2010/0021510 A1 | 1/2010 | Carreno Serraïma et al. | | |
| 2010/0281003 A1 * | 11/2010 | Jochim | .................. | G16B 15/00 707/E17.046 |
| 2013/0330335 A1 * | 12/2013 | Bremel | .................. | G16B 20/00 435/69.6 |
| 2015/0140046 A1 | 5/2015 | Ferrer Montiel et al. | | |
| 2017/0219578 A1 * | 8/2017 | Getts | .................... | G01N 33/564 |
| 2017/0219600 A1 * | 8/2017 | Alving | ............... | G01N 33/6848 |

(Continued)

FOREIGN PATENT DOCUMENTS

| | | |
|---|---|---|
| EP | 2 123 673 A1 | 11/2009 |
| EP | 2 649 985 A1 | 10/2013 |
| WO | WO 2010/115141 A2 | 10/2010 |

(Continued)

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*

(Continued)

*Primary Examiner* — Chang-Yu Wang
(74) *Attorney, Agent, or Firm* — Oblon, McClelland, Maier & Neustadt, L.L.P.

(57) ABSTRACT

The invention relates to peptides capable of inhibiting neuronal exocytosis and to products comprising such peptides, in particular pharmaceutical and cosmetic products useful for ameliorating skin conditions, disorders and/or diseases mediated by neuronal exocytosis, such as wrinkles, excessive perspiration, pruritus, cutaneous inflammation, dermatitis, atopia, psoriasis, vascular hyperreactivity, rosacea, acne, hair growth, wound healing, calluses, warts, or sensitive skin conditions, such as ulcers and lesions on the skin.

20 Claims, No Drawings

Specification includes a Sequence Listing.

(56) References Cited

U.S. PATENT DOCUMENTS

2017/0349638 A1    12/2017  Aivado

FOREIGN PATENT DOCUMENTS

| WO | WO 2010/115141 A3 | 10/2010 |
| WO | WO 2011/119484 A1 | 9/2011 |
| WO | WO 2013/040142 A2 | 3/2013 |
| WO | WO 2013/040142 A3 | 3/2013 |
| WO | WO 2017/165299 A2 | 9/2017 |
| WO | WO 2017/165299 A3 | 9/2017 |

OTHER PUBLICATIONS

Hueber, P. et al., "PMXA erschließt offen Kommunikation," 2323 Telcom Report (Siemens), No. 5, 1988, XP000000121 pp. 164-167.
International Search Report and Written Opinion issued on Oct. 15, 2019 in PCT/EP2019/065219 filed on Jun. 11, 2019.

* cited by examiner

US 12,377,035 B2

PEPTIDES FOR INHIBITING CHOLINERGIC CALCITONIN GENE-RELATED PEPTIDE (CGRP) AND ACETYLCHOLINE (ACH) RELEASE OR INHIBITING SENSITIZATION-MEDIATED BY TRPV1-MEDIATED EXCITABILITY IN SENSORY NEURONS AND METHODS OF USE THEREOF

SEQUENCE LISTING

The instant application contains a Sequence Listing which has been submitted electronically in ASCII format and is hereby incorporated by reference in its entirety. The substitute sequence listing is named "533692US_71824.ST25" which was created on Jul. 18, 2024, and is 1,592 bytes in size. It is incorporated by reference for all purposes.

FIELD OF THE INVENTION

The present invention refers to peptides capable of inhibiting neuronal exocytosis and to products comprising such peptides, in particular pharmaceutical and cosmetic products useful for ameliorating skin conditions, disorders and/or diseases mediated by neuronal exocytosis.

STATE OF THE ART

Acetylcholine (ACh) is a fast-acting, point-to-point neurotransmitter at the neuromuscular junction, in the autonomic ganglia, gland innervation and at a variety of sites within the central and peripheral nervous system. ACh Is contained in secretory vesicles of presynaptic cholinergic fibers and exocyted to the synaptic cleft acting on cholinergic postsynaptic membrane receptors. Neuronal exocytosis is an action potential-triggered and $Ca^{2+}$-dependent process driven by soluble N-ethylmaleimide-sensitive factor attachment protein receptor (SNARE) family proteins. NSF (N-ethylmaleimide-sensitive fusion protein) is a hexameric ATPase essential for all intracellular membrane traffic steps. In its role in membrane traffic, NSF is recruited to membranes by SNAPS (soluble NSF attachment proteins), which in turn are recruited by a complex of SNARE (SNAP receptor) proteins formed during membrane fusion. This complex is formed by a single vesicle SNARE, synaptobrevin or vesicle-associated membrane protein (VAMP), and two target plasma membrane SNAREs, called syntaxin and SNAP25, which are involved in vesicle docking and membrane fusion to the plasma membrane (Kasai et al., Physiol Rev., (2012), 92:1915-1964).

SNARE protein complex-mediated docking and vesicular fusion are key elements controlling any neurotransmitter secretion (Purves et al., Neuroscience, 2nd edition, (2001), as they share identical molecular mechanism. Among others and similar to ACh, serotonin, histamine, GABA, glutamate, aspartate, ATP, adrenaline, noradrenaline, dopamine, epinephrine, norepinephrine, or neuropeptides (calcitonin gene-related peptide (CGRP), substance P, neurokinins, VIP, neurotrophins, endorphins), are released through SNARE-dependent mechanism.

SNARE protein cleavage by botulinum toxins (BoNTs) disrupts vesicle fusion and neurotransmitter release (Binz et al., Toxins (Basel), (2010), 2 (4): 665-682). At molecular level, botulinum toxins BoNT/A, /C, and/E cleave SNAP-25; BoNT/B, /D, /F, and /G cleave VAMP. Only, BoNT/C is able to cleave both, SNAP25 and syntaxin (Schiavo et al., Physiol Rev. (2000); 80:717-66). Therefore, SNARE proteins have become targets for therapeutics and/or cosmetics compounds and/or products used to treat and/or prevent conditions triggered by neurotransmitter release. Indeed, botulinum toxin derived approved treatments block neurotransmitter release from presynaptic vesicles by deactivating SNARE proteins, mostly through SNAP-25 or VAMP (Zakin et al., Toxicon (2018), EP 2318033 A2, EP 1856139 A2, EP 1180524 A1, EP 2123673 A1, WO 97/34620).

The skin deeply interacts with the peripheral nervous system. Increasing evidence indicates that the neurological system directly participates in numerous skin processes. For instance, due to ACh release inhibition, the main cosmetic application of botulinum toxin derivate products is its well-known anti-wrinkle effect allowing facial muscle relaxation. Nevertheless, in the skin, cholinergic fibres provide innervation to other several annex structures within the integumentary system including sweat glands, hair follicles, blood vessels, and muscles, such as arrector pili muscles. Indeed, botulinum toxin derivatives are used experimentally in a number of dermatological conditions, which include hyperhidrosis, scar prevention, cutaneous inflammation, wound healing, facial flushing, post-herpetic neuralgia, sebum control, and itching with successful results (Kim et al., Toxins (2017), 9, 403). The general mechanism underlying these novel indications includes, in addition to ACh, the inhibition of substance P. CGRP, glutamate, and histamine release, or even mast cell activation.

For instance, skin conditions with excessive sweating, such as dyshidrotic eczema or inflammatory dermatosis, can be improved in addition to the classical thermoregulatory hyper-perspiration. The inhibition of ACh release prevents its direct action on the sweat gland and on smooth muscles surrounding the sweat glands (Swartling et al., J. Am. Acad, Dermatol. (2002), 47, 667-671; Wollina, U., J. Eur. Acad. Dermatol. Venereol. (2002), 16, 40-42). In this regard, botulinum toxin has shown beneficial effects on dermatitis or psoriasis, skin conditions that are aggravated by excessive perspiration, through reduction of local sweating (Zanchi et al., J. Eur. Acad. Dermatol. Venereol. (2008), 22, 431-436). Besides, consequent inhibition of neuropeptide release, substance P and/or CGRP, reduces associated pruritus and vasodilatation (Humm et al, Exp. Neurol. (2000), 161, 361-372, Ishikawa. et al., Jpn. J. Opthalmol. (2000), 44, 106-109), which causes discomfort and the worse the symptoms.

Inhibition of neuronal exocytosis diminishes and prevents pruritus in several conditions and through different molecular mechanisms. ACh mediates itch in pruritic skin conditions such as atopic dermatitis (Hallett M., Ann. Neurol. (2000), 48, 7-8). Substance P is associated to itch and flare through histamine release via mast cell activation, while CGRP through vasodilatation. Therefore, corresponding neurotransmitter release disruption by botulinum toxin reduces itch sensation, histaminergic as well as non-histaminergic type (Gazerani et al., Br. J. Dermatol. (2009), 161,737-745). Pruritogenic itching is accompanied by skin inflammation, and suppression of neuronal exocytosis decreasing neurogenic inflammation, so itching in atopic dermatitis and psoriasis is reduced (Han et al., Dermatol, Surg. (2017); Ward et al., J. Investig. Dermatol. (2012), 132, 1927-1930; Saber et al., Arch. Dermatol. (2011), 147, 629-630; Gilbert et al., J. Drugs Dermatol. (2014), 13, 1407-1408; Gazerani et al., Br. J. Dermatol. (2009), 161,737-745; Cao et al., Neuroreport. (2017), 28, 518-526; Ramachandran et al., Toxins (2018), 10, pii: E134). Similarly, inflammatory skin dermatosis such as rosacea characterized by facial flush and erythema are improved through blockade of ACh, Substance P and CGRP release, as cutaneous vasodilatation and skin local inflammation are reduced. (Eshghi et al., Acta Med. Iran (2016), 54, 454-457; Bloom et al., Dermatol. Surg. (2015), 41 (Suppl. 1), S9-S16; Geddoa et al., Int. J. Dermatol. (2013), 52, 1547-1550; Odo et al., Dermatol, Surg. 2011, 37, 1579-1583).

In skin appendixes, such as sebaceous glands, ACh increases lipid synthesis in sebocytes, and botulinum toxin significantly lowers sebum production in humans (Min et al., Aesthet. Surg. J. (2015), 35, 600-610; Rose, et al., Dermatol. Surg. (2013), 39, 443-448). Therefore, arrector pili muscles and local muscarinic receptors on sebaceous glands are targets for the neuro-modulatory regulation through ACh release inhibition.

Finally, inhibition of ACh release can be used to prevent and manage healing, and/or to control symptoms of hypertrophic scars, Reduction of local ACh release, immobilizes muscles surrounding healing tissue and reduces skin tension. This process relieves trapped nerve fibres in the keloid neutralizing associated itching (Uyesugi et al., Am J Phys Med Rehabil. (2010), 89 (2): 153-155). In this regard, botulinum toxin has shown to inhibit fibroblast proliferation, transforming growth factor beta, collagen I and III, myosin II and a-smooth muscle acting in the keloid fibroblast (Xiao et al., Aesthet. Plast. Surg. (2011), 35, 802-807; Chen et al., Ann. Plast, Surg. 2016, 77, e46-e49; Jeong al., Plast, Reconstr. Surg. (2015), 136, 171e-178e; Wang, X. et al., Aesthet. Surg. J. (2014). 34, 154-159. Based on this, the potential effects of neuronal exocytosis blockade on the scar surrounding muscles and fibroblast suggest its use for wound healing and scar prevention.

Thus, overall, inhibition and/or modulation of neurotransmitter release is useful, not only for facial wrinkles and motor muscle dysfunctions, but also to prevent, treat or care novel skin-related conditions such as excessive perspiration, pruritus, cutaneous inflammation, dermatitis, atopia, psoriasis, vascular hyperreactivity, rosacea, acne, hair growth, wound healing, calluses, warts, or sensitive skin conditions, such as ulcers and lesions on the skin.

Botulinum toxin derived treatments require repeated injections and can cause an immune reaction losing efficacy. Other side effects are cephalalgias, nausea, paralysis or muscle weakness and respiratory failure. In addition, lability and pharmaceutical preparation instability make them a high cost treatments. Thus, development of simpler and more stable molecular structures to substitute them is required. For this purpose, peptides derived from the primary structure of SNARE core complex proteins are capable to disrupt neurotransmitter release.

A synthetic hexapeptide derived from the primary structure of the amino terminal fragment of SNAP25 is widely used in treatment and prevention of expression wrinkles as described in EP1180524A1 and EP2123673A1. This peptide flips across the membrane and specifically interferes with SNAP25, thus Impairing SNARE complex assembly and neurotransmitter exocytosis.

Similarly, peptides derived from the carboxy terminal region of SNAP25, or from synaptobrevin or syntaxin were also designed to inhibit neuronal exocytosis as described in WO97/34620. However, they must have a minimum length of 20 amino acids and a maximal length of 28 for optimum activity. Therefore, their large size increases production costs and difficult later development as cosmetic and/or therapeutic agents.

Other peptides, not directly derived from SNARE core-complex proteins with unknown mechanism, are claimed to reduce neuronal exocytosis as described in WO2013153192A1 and WO2013070808A1. Likewise, peptides derived from the subunit C of the membrane component V-ATPase are described in WO2011/048443 as neuronal exocytosis inhibitors by targeting synaptobrevin and showing a potential anti-wrinkle effect.

U.S. Pat. No. 6,169,074 to Montal, et al. discloses combinations of peptides that interfere with the SNARE complex within the synaptic gap on the neuromuscular junction.

U.S. Pat. No. 6,866,856 to Lu, et al. describes limonoids (alkaloid extracts of citrus fruits) that inhibit acetylcholine release at the neuromuscular junction of skeletal muscle.

U.S. Pat. No. 7,566,464 to Belfer teaches a skin care composition that improves the appearance of expression lines of the human face. This product comprises an extract of *Acmella oleracea* which rapidly relaxes the contractile muscle elements and suppresses the action of the expressive facial muscle based on the synergy of strengthening the dermis and inhibiting the muscle tissues related to expression lines.

U.S. Pat. No. 7,015,192 to Blanes, et al. discovers that peptides derived from the N-terminal of protein SNAP-25 within the SNARE complex inhibit acetylcholine release. The principle molecule, acetyl hexapeptide-8 (also formally named acetyl hexapeptide-3 or ARGIRELINE®) is claimed to compete with the efficacy of Botulinum toxin but reducing administration-derived risks and production cost.

There are annex molecules that regulate SNARE complex which are also important in neuronal exocytosis. For instance, Snapin is a SNAP25-binding protein, which stabilizes the coupling between synaptotagmin 1 and the SNARE complex during $Ca^{2+}$-triggered exocytosis (Ilardi et al., Nat Neurosci. (1999) 2:119-124; Buxton et al., Biochem. J. (2003) 375, 433-440). Deletion of Snapin does not fully eliminate neurotransmitter release, but rather reduces excitatory postsynaptic currents by 70% (Pan et al., Neuron. (2009) 61:412-424), suggesting Snapin as a non-essential modulator in neuronal exocytosis. Recombinant Snapin carboxy terminal blocked the association of the SNARE complex with synaptotagmin. Indeed, peptides derived from Ct-Snapin sequence disrupted SNARE complex assembly, impairing neuronal exocytosis (Ilardi et al., Nat Neurosci. (1999), 2:119-124). Only four 20-mer peptide fragments corresponding to C-terminal coiled-coil domain only derived from position 117 to 136 inhibited exocytosis. Therefore, Snapin is a potential target to design exocytosis regulators rather than full inhibitors, probably reducing undesired effects of more potent treatments.

In conclusion, this innovation provides an alternative to the existing necessities and encompasses novel peptide sequences identification, which are able to reduce neuronal exocytosis.

SUMMARY OF THE INVENTION

The Applicant has surprisingly found peptides able to inhibit, or at least reduce, the release of neurotransmitters, in particular acetylcholine, and the neuropeptide CGRP, from neurons.

Even if the exact molecular mechanism has not yet fully elucidated and confirmed, and without being bound by any theory, the inventors believe that inhibition or reduction of exocytosis can be due to indirect modulation of SNARE complex formation though disruption of SNAP25 interaction.

The Applicant has found that the peptides having the following sequences nos. 1 to 5 have a neuronal exocytosis blocking effect and consequently such peptides are able to inhibit, or at least reduce, the release of acetylcholine from the peripheral nerve endings.

```
                                  SEQ ID NO: 1
         HYWRELQYR

SEQ ID NO: 2
         MQVWLRMWIDYRAT

SEQ ID NO: 3
         RRVVLVNNIL

SEQ ID NO: 4
         LRVQMVNMFL

SEQ ID NO: 5
         WEQEFLRR
```

The Applicant has also found that the neuronal exocytosis blocking effect is also obtained with sequences having a length of not more than 20 amino acids and comprising the above described SEQ ID NOS: 1 to 5, or a sequence having at least 70%, preferably at least 80%, and more preferably at least 90% sequence identity with any one of SEQ ID NOS: 1 to 5.

The Applicant has also found that the neuronal exocytosis blocking effect can be modulated by linking to the N-terminus of the above described SEQ ID NOS: 1 to 5 an alkyl carbonyl group, such as, for example, an acetyl group, a palmitoyl group, or a myristoyl group as well as by forming a salt of the above described SEQ ID NOS: 1 to 5 with a suitable anion, such as, for example, chloride, acetate or trifluoroacetate.

Accordingly, a first aspect of the present invention relates to peptides having length equal to or lower than 20 amino acids, preferably equal to or lower than 15 amino acids, and comprising any one of the SEQ ID NOS: 1 to 5, or a sequence having at least 70%, preferably at least 80%, and more preferably at least 90% sequence identity with any one of the SEQ ID NOS: 1 to 5, and a derivative or salt thereof.

A second aspect of the present invention relates to a pharmaceutical or cosmetic composition comprising (I) a peptide having length equal to or lower than 20 amino acids, preferably equal to or lower than 15 amino acids, and comprising any one of the. SEQ ID NOS: 1 to 5, or a sequence having at least 70%, preferably at least 80%, and more preferably at least 90% sequence identity with any one of the SEQ ID NOS: 1 to 5, and a derivative or salt thereof, and (ii) at least one pharmaceutically or cosmetically acceptable ingredient.

A third aspect of the present invention relate to the use of a peptide having length equal to or lower than 20 amino acids, preferably equal to or lower than 15 amino acids, and comprising any one of the SEQ ID NOS: 1 to 5, or a sequence having at least 70%, preferably at least 80%, and more preferably at least 90% sequence identity with any one of the SEQ ID NOS: 1 to 5, and a derivative or salt thereof, for ameliorating skin conditions, disorders and/or diseases mediated by neuronal exocytosis.

A fourth aspect of the present invention relates to a therapeutic or non-therapeutic method for ameliorating skin conditions, disorders and/or diseases mediated by neuronal exocytosis comprising the topical application of a pharmaceutical or cosmetic composition comprising (i) a peptide having length equal to or lower than 20 amino acids, preferably equal to or lower than 15 amino acids, and comprising any one of the SEQ ID NOS: 1 to 5, or a sequence having at least 70%, preferably at least 80%, and more preferably at least 90% sequence identity with any one of the SEQ ID NOS: 1 to 5, and a derivative or salt thereof, and (ii) at least one pharmaceutically or cosmetically acceptable ingredient.

More in particular, skin conditions, disorders and/or diseases mediated by neuronal exocytosis include wrinkles, excessive perspiration, pruritus, cutaneous inflammation, dermatitis, atopia, psoriasis, vascular hyperreactivity, rosacea, acne, hair growth, wound healing, calluses, warts, or sensitive skin conditions, such as ulcers and lesions on the skin.

A further aspect of the present invention relates to a polynucleotide that codes a peptide having length equal to or lower than 20 amino acids, preferably equal to or lower than 15 amino acids, and comprising any one of the SEQ ID NOS: 1 to 5, or a sequence having at least 70%, preferably at least 80%, and more preferably at least 90% sequence identity with any one of the. SEQ ID NOS: 1 to 5.

DETAILED DESCRIPTION OF THE INVENTION

According to a first aspect, the present invention relates to peptides having length equal to or lower than 20 amino acids, preferably equal to or lower than 15 amino acids, and comprising any one of the SEQ ID NOS: 1 to 5, or a sequence having at least 70%, preferably at least 80%, and more preferably at least 90% sequence identity with any one of the SEQ ID NOS: ID 1 to 5, and a derivative or salt thereof.

Preferably, the present invention relates to a peptide having length equal to or lower than 20 amino acids, preferably equal to or lower than 15 amino acids, more preferably equal to or lower than 10 amino acids, and comprising SEQ ID NO: 1, or a sequence having at least 70%, preferably at least 80%, and more preferably at least 90% sequence identity with SEQ ID NO: 1, and a derivative or salt thereof.

Preferably, the present invention relates to a peptide having length equal to or lower than 20 amino acids, preferably equal to or lower than 15 amino acids, and comprising. SEQ ID NO: 2, or a sequence having at least 70%, preferably at least 80%, and more preferably at least 90% sequence identity with SEQ ID NO: 2, and a derivative or salt thereof.

Preferably, the present invention relates to a peptide having length equal to or lower than 20 amino acids, preferably equal to or lower than 15 amino acids, more preferably equal to or lower than 10 amino acids, and comprising SEQ ID NO: 3, or a sequence having at least 70%, preferably at least 80%, and more preferably at least 90% sequence identity with SEQ ID NO: 3, and a derivative or salt thereof.

Preferably, the present invention relates to a peptide having length equal to or lower than 20 amino acids, preferably equal to or lower than 15 amino acids, more preferably equal to or lower than 10 amino acids, and comprising SEQ ID NO: 4, or a sequence having at least 70%, preferably at least 80%, and more preferably at least 90% sequence identity with SEQ ID NO: 4, and a derivative or salt thereof.

Preferably, the present invention relates to a peptide having length equal to or lower than 20 amino acids, preferably equal to or lower than 15 amino acids, more preferably equal to or lower than 10 amino acids, and comprising SEQ ID NO: 5, or a sequence having at least 70%, preferably at least 80%, and more preferably at least 90% sequence identity with SEQ ID NO: 5, and a derivative or salt thereof.

To the best knowledge of the named inventors and applicant of the present application, none of the peptides described herein is known in the art before the priority of the present application. However, any peptide known in the art before the priority date of the present application falling within the scope of the present Invention is herein properly disclaimed.

Abbreviations of the amino acid sequences used herein are in accordance with the IUPAC-IUB nomenclature as reported in the following Table A.

TABLE A

| Alanine | Ala | A | Arginine | Arg | R |
| Asparagine | Asn | N | Aspartic acid | Asp | D |
| Cysteine | Cys | C | Glutamic acid | Glu | E |
| Glutamine | Gln | Q | Glycine | Gly | G |
| Histidine | His | H | Isoleucine | Ile | I |
| Leucine | Leu | L | Lysine | Lys | K |
| Methionine | Met | M | Phenylalanine | Phe | F |
| Proline | Pro | P | Serine | Ser | S |
| Threonine | Thr | T | Tryptophan | Trp | W |
| Tyrosine | Tyr | Y | Valine | Val | V |

"Percentage sequence identity" with respect to a peptide sequence refers to the percentage of residues that are identical in two sequences. The percent sequence identity (% SI) is calculated by the following formula:

$$\% SI = (nt-nd) \times 100/nt$$

wherein nt is the number of residues in the basic sequence and nd is the total number of non-identical residues in the confronted sequence when aligned so that a maximum number of amino acids are identical. Accordingly, a sequence RKVVLVNQIL (SEQ ID NO: 6) will have a sequence identity of 80% with the sequence of SEQ ID NO: 3 RRVVLVNNIL (nd=2 and nt=10).

Peptide according to the invention may have at least 70%, at least 75%, at least 80%, at least 85%, at least 90% and at least 95% sequence identity to a reference sequence when optimally aligned. Optimal alignment of the sequences may be conducted by various known methods and computerized implementation of known algorithms (e.g. BLAST, TFASTA, BESTFIT, such as in the Wisconsin Genetics Software Package, Release 7.0, Genetics Computer Group, Madison, WI). The BLAST algorithm (Altschul et al., Mol. Biol. (1990), 215, 403-410) for which software may be obtained through the National Center for Biotechnology Information www.ncbi.nlm.nih.gov/) may also be used.

Variation of the amino acid sequence in the peptides comprising the SEQ ID NOS: 1 to 5 of the present invention comprises conservative substitution of amino acids that do not influence peptide activity. The substitutions able to maintain the peptide activity are selected on the basis of (a) the efficacy in maintaining the structure of the peptide backbone in the area of substitution, such as sheet or helical three-dimensional structures, (b) the efficacy in maintaining electrical charge or hydrophobicity of the molecule in the target area, or (c) the efficacy of maintaining the bulk of the side chain.

Amino acids are classified according to general side chain properties as described in the following Table B.

TABLE B

| hydrophobicity | NorLeucine, Met, Ala, Val, Leu, Ile; |
| neutral hydrophobicity | Cys, Ser, Thr; |
| acidity | Asp, Glu; |
| basicity | Asn, Gln, His, Lys, Arg; |
| residue that affects chain orientation | Gly, Pro; |
| aromaticity | Trp, Tyr, Phe. |

Examples of conservative substitution belong to the group consisting of basic amino acids (arginine, lysine and histidine), acidic amino acids (glutamic acid and aspartic add), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine, and threonine).

The amino acid substitutions that do not generally alter the specific activity are known in the art of the present invention.

Most common occurred alteration are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations. Another example of conservative substitutions are shown in the following Table C.

TABLE C

| Starting amino acid | Possible substitution | Preferred substitution |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norLeucine | Leu |
| Leu (L) | norLeucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norLeucine | Leu |

The peptide of the present invention may be in the form of a modified peptide, of which N- or/and C-terminal is chemically modified or protected with organic compounds.

The term "derivative" or "derivative thereof" as employed herein in relation to a peptide of the present invention means a peptide wherein the N- and/or C-terminal thereof is chemically modified or protected with an organic compound.

Examples of modification include phosphorylation, glycosylation, acylation (including acetylation, lauroylation, myristorylation, palmitoylation), alkylation, carboxylation, hydroxylation, glycation, biotinylation, ubiquitinylation, and amidation.

Preferably, the peptide of the present invention may be modified at the N-terminal thereof, more preferably by acylation, including acetylation, lauroylation, myristorylation, and palmitoylation. N-terminal acetyl and palmitoyl peptide derivatives are a preferred aspect of the present invention.

The term "salt" or "salt thereof" as employed herein in relation to a peptide of the present invention means a salt of a peptide or derivative thereof with a suitable acid or base.

Typical examples of acids include, for example, hydrochloric acid, acetic acid, trifluoroacetic acid, oxalic acid, maleic acid, methanesulfonic acid, para-toluenesulfonic acid, succinic acid, citric acid, tartaric acid, and lactic acid.

Typical examples of bases include for example, mono-, di- and trialkylamines, for instance methylamine, dimethylamine, trimethylamine, ethylamine, diethylamine, triethylamine, propylamine, dipropylamine, tripropylamine, ethylenediamine, mono-, di- and trialkanolamines, for instance monoethanolamine, diethanolamine and triethanolamine; guanidine, morpholine, piperidine, pyrrolidine, piperazine, 1-butylpiperidine, 1-ethyl-2-methyl-piperidine, N-methylpiperazine, 1,4-dimethylpiperazine, N-benzylphenylethylamine, N-methylglucosamine, and tris(hydroxymethyl)aminomethane.

An acetate or trifluoroacetate salt of a peptide, or a derivative thereof, is preferably employed under the present invention.

Depending on its length, the peptide of the present invention may be synthesized by a method well known in the art, for example, by an automated peptide synthesizer, or produced by a genetic engineering technology. For example, a fusion gene encoding a fusion protein including a fusion partner and the peptide of the present invention is prepared by genetic engineering, and then transformed into a host cell to express the fusion protein. Thereafter, the peptide of the present invention is cleaved and isolated from the fusion protein using a protease or a compound so as to produce the desired peptide. To this end, a DNA sequence encoding amino acid residues which can be cleaved by a protease such as Factor Xa or enterokinase, or a compound such as CNBr or hydroxylamine may be inserted between the polynucleotides encoding the fusion partner and the peptide of the present invention.

The peptides of the present invention may exist as stereoisomers or mixtures of stereoisomers; for example, the amino acids that make them up can have L-configuration, D-configuration or be racemic independently from each other. Therefore, It is possible to obtain isomeric mixtures as well as racemates or diastereomeric mixtures or pure diastereomers or enantiomers, depending on the number of asymmetric carbons and what isomers or isomeric mixtures are present. The preferred structures of the peptides of the present invention are pure isomers, i.e., enantiomers or diastereomers. The most preferred structures of the peptides of the present invention include amino acids having the L-configuration. Unless otherwise indicated, it is understood that when it is indicated that one amino acid can be Ala, it is understood that it is selected from L-Ala-, D-Ala- or racemic or non-racemic mixtures of both.

The cosmetic composition of the present invention comprises at least one of the above described peptides together with at least one cosmetically acceptable ingredient.

The pharmaceutical composition of the present invention comprises at least one of the above described peptides together with at least one pharmaceutically acceptable ingredient.

The pharmaceutical or cosmetic composition of the present invention can comprise an amount of the peptide, or a derivative and/or salt thereof, ranging from 0.00000001% to 20% by weight, preferably from 0.000001% to 15% by weight, more preferably from 0.0001% to 10% by weight, and even more preferably from 0.0001% to 5% by weight.

The cosmetic composition of the present invention can contain a variety of other optional components suitable for rendering such compositions more cosmetically or aesthetically acceptable or to provide them with addition usage benefits. Such conventional optional ingredients are well-known to those skilled in the art. These include any cosmetically acceptable ingredients such as those found in the CTFA International Cosmetic Ingredient Dictionary and Handbook, 7th edition, edited by Wenninger and McEwen, (The Cosmetic, Toiletry, and Fragrance Association, Inc., Washington, D.C., 1997). As used herein "cosmetically acceptable" means a material (e.g., compound or composition) which is suitable for use in contact with skin, hair or other suitable substrate as defined hereinbelow.

Cosmetically acceptable ingredients useful in the present invention includes cosmetically acceptable carriers, volatile and non-volatile solvents, water, and other additional ingredients, such as surfactants, preservatives, absorbents, chelating agents, lubricants, moisturizers water repellents, anti-oxidants, UV absorbers, anti-irritants, vitamins, trace metals, anti-microbial agents, perfumes, dyes and colour ingredients, and/or structuring agents.

The expression "cosmetically acceptable carrier", as used herein, means one or more compatible solid or liquid fillers, diluents, extenders and the like, which are cosmetically acceptable as defined hereinabove. The term "compatible", as used herein, means that the components of the compositions of this invention are capable of being combined with the primary actives of the present invention, and with each other, in a manner such that there is no interaction which would substantially reduce the efficacy of the composition under ordinary use situations.

The type of carrier utilized in the present invention depends on the type of product desired. The compositions useful in the present invention may be a wide variety of product forms. These include, but are not limited to, lotions, creams, gels, sticks, sprays, ointments, pastes, mousses and cosmetics (e.g., solid, semi-solid, or liquid make-up, including foundations).

These product forms may comprise several types of carriers including, but not limited to, solutions, aerosols, emulsions (including oil-in-water or water-in-oil), gels, solids, and liposomes.

The compositions of the present invention may comprise water, in different amounts depending on the form of the composition. The amount of water, if present, can range from less than 1% to more than 99% by weight with respect to the weight of total composition. The aqueous composition of the present invention are especially formulated as aqueous lotions or as water-in-oil or oil-in-water emulsions or as multiple emulsions (oil-in-water-in-oil or water-in-oil-in-water triple emulsion). Such emulsions are known and described, for example, by C, FOX in "Cosmetics and Toiletries"-November 1986-Vol. 101-pages 101-112.

Solid compositions, spray compositions, and water-in-oil creams usually comprise amounts of water lower than 10%, more preferably lower than 5% by weight with respect to the total weight of the composition. Roll-on compositions, aqueous compositions, and deodorant usually comprises amount of water of from about 15% to about 99%, more preferably from about 30% to about 90%, even more preferably about 50% to about 80%, by weight with respect to the total weight of the composition.

The compositions of the present invention may also comprise silicones. If present, the silicones will generally be at a level of from about 30% to about 85%, more preferably from about 40% to about 75%, even more preferably about 50% to about 65%, by weight with respect to the total weight of the composition.

The silicones useful herein are preferably linear or cyclic silicones having from 2 to 7 silicone atoms, these silicones being optionally substituted with alkyl or alkoxy groups of 1 to 10 carbon atoms. Suitable silicones include dodecamethylcyclohexasiloxane, cyclopentasiloxane, decamethylcyclopenta siloxane, cyclotetrasiloxane, heptamethyloctyltrisiloxane, hexamethyldisiloxane, decamethyltetrasiloxane, dodeca-methylpentasiloxane octamethyltetrasiloxane and mixtures thereof.

The compositions of the present invention may comprise one or more volatile solvent. If present, the volatile solvent or mixture of solvents will generally be at a level of from about 10% to about 90%, more preferably from about 25% to about 75%, even more preferably about 35% to about 65%, by weight with respect to the total weight of the composition. The solvents useful herein are preferably organic volatile solvents.

As used herein, "volatile" refers to substances with a significant amount of vapour pressure under ambient conditions, as is understood by those in the art.

The volatile solvents for use herein will preferably have a vapour pressure of about 2 kPa or more, more preferably about 6 kPa or more, at 25° C. The volatile solvents for use herein will preferably have a boiling point under normal atmosphere (1 atm) of less than about 150° C., more preferably less than about 100° C., even more preferably less than about 90° C., even more preferably still less than about 80° C.

Preferably, the volatile solvents for use herein will be relatively odourless and safe for use on human skin. Suitable volatile solvents include, but are not limited to C1-C4 alcohols, volatile silicones and mixtures thereof. Preferred volatile solvents are C1-C4 alcohols and mixtures thereof. More preferred for use herein is ethanol.

The compositions of the present invention may also comprise one or more non-volatile solvent. If present, the non-volatile solvent or mixture of solvents will generally be at a level of from about 1% to about 20%, more preferably from about 2% to about 10%, even more preferably from about 3% to about 5%, by weight with respect to the total weight of the composition. Suitable non-volatile solvents include, but are not limited to, benzyl benzoate, cetearyl alcohol, cetyl alcohol, diethyl phthalate, isopropyl myristate, dimethicone, caprylylmethicone, and mixtures thereof.

Several other additional ingredients can be present in the compositions of the present invention. These include, but are not limited to, hydrophilic polymers selected from polyethylene glycols (PEGs), polyvinylpyrrolidones (PVP), hydroxypropyl methylcellulose (HPMC) and poloxamers; UV stabilizers such as benzophenone-3; antioxidants such as tocopheryl acetate; preservatives such phenoxyethanol, benzyl alcohol, methyl paraben, propyl paraben; pH as adjusting agents such as lactic acid, citric acid, sodium citrate, succinic acid, phosphoric acid, sodium hydroxide, sodium carbonate; deodorants and anti-microbials, such as farnesol, zinc phenolsulphonate, and ethylhexylglycerin; humectants such as tribehenin, glycerine; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; propellants such as propane, isopropane, butane, and isobutene; salts in general, such as potassium acetate and sodium chloride and mixtures thereof; perfumes and dyes.

If present, these additional ingredients will preferably be present at a level of less than 10%, more preferably of less than 5%, by weight with respect to the total weight of the composition.

Preferably, the pharmaceutical composition of the present invention is prepared in suitable dosage forms comprising an effective amount of at least one of the above described peptides together with at least one pharmaceutically acceptable ingredient.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions. Other suitable dosage forms are those with sustained release and those based on liposomes for oral, injectable or transdermal administration.

As described herein, the pharmaceutical composition of the present invention comprises at least one of the above described peptides together with a pharmaceutically acceptable excipient, which, as used herein, includes any and all solvents, diluents, or other vehicle, dispersion or suspension aids, surface active agents, Isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; Isotonic saline; Ringer's solution; ethyl alcohol, and phosphate buffer solutions, other non-toxic compatible lubricants such as sodium lauryl sulfate and magnesium stearate, coloring agents, releasing agents, coating agents, sweetening, flavoring and perfuming agents, preservatives and antioxidants.

The terms "pharmaceutically acceptable" and "physiologically acceptable" are intended to define, without any particular limitation, any material suitable for preparing a pharmaceutical composition to be administered to a living being.

The dosage forms can also contain other traditional ingredients such as: preservatives, stabilizers, surfactants, buffers, salts for regulating osmotic pressure, emulsifiers, sweeteners, colorants, flavourings and the like.

The pharmaceutical compositions of this invention may be administered orally, parenterally, by inhalation spray, topically, rectally, nasally, buccally, vaginally or via an implanted reservoir. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions of this invention may also be administered by nasal aerosol or inhalation or delivered by implantation (e.g., surgically), such as with an implantable or indwelling device like a stent.

The dosage forms of the pharmaceutical composition of the present invention can be prepared by techniques that are familiar to a pharmaceutical chemist, and comprise mixing, granulation, compression, dissolution, sterilization and the like.

The peptides of the present invention are able to inhibit, or at least reduce, the release of neurotransmitters, in particular acetylcholine, and of the neuropeptide CGRP, from neurons.

Accordingly, a further aspect of the present invention relate to the use of at least one of the above described peptides, and a derivative or salt thereof, for ameliorating skin conditions, disorders and/or diseases mediated by neuronal exocytosis.

As discussed above, this property can be used not only for the treatment of facial wrinkles and motor muscle dysfunctions, but also to reduce, prevent or for the care of several skin-related conditions in which neuronal vesicle release are involved such as excessive perspiration, pruritus, cutaneous inflammation, dermatitis, atopia, psoriasis, vascular hyperreactivity, rosacea, acne, hair growth, wound healing, calluses, warts, or sensitive skin conditions, such as ulcers and lesions on the skin.

In other words, skin conditions, disorders and/or diseases mediated by neuronal exocytosis include facial wrinkles, motor muscle dysfunctions, excessive perspiration, pruritus, cutaneous inflammation, dermatitis, atopia, psoriasis, vascular hyperreactivity, rosacea, acne, hair growth, wound healing, calluses, warts, or sensitive skin conditions, such as ulcers and lesions on the skin, and the like.

Accordingly, the present invention also relates to a therapeutic or non-therapeutic method for ameliorating skin conditions, disorders and/or diseases mediated by neuronal exocytosis, in particular for reducing wrinkles, excessive perspiration, pruritus, cutaneous inflammation, dermatitis, atopia, psoriasis, vascular hyperreactivity, rosacea, acne, hair growth, wound healing, calluses, warts, or sensitive skin conditions, such as ulcers and lesions on the skin, comprising the topical application of a pharmaceutical or cosmetic composition comprising (i) at least one of the above described peptides, and a derivative or salt thereof, and (ii) at least one pharmaceutically or cosmetically acceptable ingredient.

A further aspect of the present invention relates to a polynucleotide that codes at least one of the above described peptides.

The polynucleotide mentioned above enables production of the peptides of the present invention in large quantities. For example, cultivation of vectors that include polynucleotides encoding peptides allows production of peptides in large quantities.

A polynucleotide is a nucleic acid molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those.

The following examples are intended to better illustrate the present invention without however limiting it.

EXAMPLES

Example 1: Chemical Synthesis

All peptides were synthetized with the C terminus amidated using the standard Fmoc solid-phase method (Perez de la Vega et al., Molecules (2010), 15:4924-4933; Behrendt et al., J. Pept. Sci. (2016), 22(1):4-27; Mäde et al., Beilstein J. Org. Chem. (2014), 10:1197-1212). Synthesis of the peptides of invention, mixtures and/or their cosmetically acceptable salts can be carried out according to the conventional methods, known in the prior art, such as solid phase peptide synthesis methods, enzymatic synthesis or any combination (Bondazky et al., Int. J. Pept. Protein Res. (1993), 42(1): 10-3).

All synthetic processes were carried out with Kromasil-C18-HPLC (5 µm, 4.6×250 mm). After, peptides were eluted with linear gradients of acetonitrile ($CH_3CN$) with trifluoroacetic acid (TFA) (gradient: 5-55% B in 2 min, flow: 1 ml/min, eluent A: 100% $H_2O$+0.1% TFA; eluent B: 100% $CH_3CN$+0.1% TFA). Peptides detection was performed by measuring absorbance at 220 nm. The Fmoc group was removed with 20% piperidine/DMF solution for 30 min reaction. Washes between stages were carried out with DMF (5 times). All synthetic reactions and washes were performed at 25° C. HPLC analysis of the obtained peptides showed a purity exceeding 80% in all cases. The identity of the peptides obtained was confirmed by ESI-MS.

Process for introducing the Nt-acetyl group onto the peptidyl resins: 1 mmol (1 equiv) of the peptidyl resins was treated with 25 equiv of pre-dissolved acetic anhydride in the presence of 25 equiv of DIEA, using 5 mL of DMF as solvent. After 30 min reaction, peptide resins were washed with DMF (1 min×5), DCM (1 min×4), and diethyl ether (1 min×4). Finally, peptidyl resins were dried under vacuum.

Process for introducing the Nt-palmitoyl group onto the peptidyl resins: 3 mmol (3 equiv) of pre-dissolved palmitic acid were incorporated onto peptidyl resins, in the presence of 3 equiv of HTBU and 6 equiv of NMM. They were allowed to react for 30-60 minutes using DMF as reagent. Afterwards, resins were washed 3 times with DMF Cleavage process from the polymeric support of the peptidyl resins: Dried peptidyl resins were treated with TFA:TIS:$H_2O$ (95:2.5:2.5) for 2 hours at 25° C. under vibration.

Example 2: Inhibition of CGRP Release on Cultured Sensory Neurons by the Peptides of Invention The induction of the release of calcitonin-gene related peptide (CGRP) with capsaicin enables direct measurement of neuronal exocytosis (Meng J. et al., J. Cell. Sci. (2007) 15; 120(Pt 16):2864-74, and Meng J. et al., Mol. Neurobiol. (2014); 50(2):574-88).

The tested peptides were evaluated by measuring their capability of inhibiting CGRP induced-release on peptidergic sensory neurons. Dorsal root ganglia were seeded (50.000 cells/well) in a 96-well plate previously coated with poly-L-lysine and laminin. After 48 hours seeding, cells were incubated with Hank's Balanced salt solution containing peptides of invention at 20, 50 or 100 µM for 1 hour. Next, cells were stimulated for 10 min with 1 µM capsaicin at 37° C. Then, CGRP content was determined in supernatants using colorimetric based CGRP EIA (Spi-Bio Inc) following manufacturer's instructions. Absorbance measurements (405 nm) were standardized with regard to the maximum signal detected with capsaicin stimulation in vehicle treated cells. Inhibition values of CGRP release were calculated as percentages by considering maximum signal to capsaicin-induced release and minimum as non-stimulated cells. Table D details inhibition values of M3 activity inhibition obtained for the peptides of invention.

TABLE D

| Peptide | Sequence | Nt-Derivatization | % CGRP release 100 μM | 50 μM | inhibition 20 μM |
|---|---|---|---|---|---|
| SEQ ID NO: 1 | HYWRELQYR | acetyl | 39.1 | | 10.1 |
| SEQ ID NO: 2 | MQVWLRMWIDYRAT | acetyl palmitoyl | 55.3 | 53.9 | 49.3 35.5 |
| SEQ ID NO: 3 | RRVVLVNNIL | palmitoyl | | 74.8 | 34.0 |
| SEQ ID NO: 4 | LRVQMVNMFL | acetyl | 77.4 | | 14.2 |

Peptides inhibited capsaicin-induced CGRP release in a range of 10-50% at 20 UM, 50-75% at 50 UM for Nt-palmitoylated, and 40-77% at 100 UM for Nt-acetylated.

Example 3: Inhibition of Acetylcholine Release in a Neuroblastoma Cell Line by the Peptides of Invention To determine the compound of the invention effects on acetylcholine release, a human neuroblastoma cell line (50.000 cells/well) was used. Cells were differentiated to cholinergic neuronal phenotype for 4 days. Then, cells were pre-incubated for 60 minutes with the compounds (between 0.1 and 100 μM) as acetyl- or palmitoyl-form and conjugated with trifluoroacetate (TFA) or acetate salt. Afterwards, acetylcholine release was induced by membrane depolarization evoked by 15 minutes incubation with 50 mM KCl. Acetylcholine level in supernatants was quantified by using Amplex® Red Acetylcholine Assay Kit (Thermofisher) following manufacturer's instructions. Acetylcholine is enzymatically transformed producing $H_2O_2$, which resulted in a quantifiable fluorescent signal. Fluorescence (Ex 530 nm/Em 590 nm) was measured in FluorStar equipment. Acetylcholine content was normalized to the total protein content using BCA assay (Pierce) following manufacturer's instructions. Fluorescence measurements were normalized to the maximum signal detected with KCl stimulation in vehicle treated cells. Vesicle exocytosis disruption by the compounds of the invention lead to a decrease of acetylcholine release (Table E).

TABLE E

| Peptide | Sequence | Nt-Derivatization | μM | % Ach release inhibition TFA | Acetate |
|---|---|---|---|---|---|
| SEQ ID NO: 1 | HYWRELQYR | acetyl | 100 | 65.9 | — |
| | | | 50 | 33.6 | — |
| | | | 10 | 87.9 | 55.9 |
| | | | 1 | — | 27.9 |
| | | | 0.1 | — | 42.2 |
| | | palmitoyl | 50 | 75.9 | — |
| | | | 10 | 49.4 | 87.5 |
| | | | 5 | 7.9 | — |
| | | | 1 | — | 81.3 |
| | | | 0.1 | — | 42.9 |
| SEQ ID NO:. 2 | MQVWLRMWIDYRAT | acetyl | 20 | 10.9 | — |
| | | | 10 | 78.8 | 55.8 |
| | | | 5 | 76.2 | — |
| | | | 1 | — | 41.0 |
| | | | 0.1 | — | 39.6 |
| | | palmitoyl | 50 | 20.6 | — |
| | | | 10 | -35.1 | — |
| | | | 5 | -46.1 | — |
| SEQ ID NO: 3 | RRVVLVNNIL | palmitoyl | 50 | 82.8 | — |
| | | | 10 | 81.8 | 86.7 |
| | | | 5 | 75.4 | — |
| | | | 1 | — | 92.5 |
| | | | 0.1 | — | 57.0 |
| SEQ ID NO: 4 | LRVQMVNMFL | acetyl | 100 | 6.8 | — |
| | | | 50 | 58.9 | — |
| | | | 10 | 84.3 | — |
| | | palmitoyl | 50 | 83.0 | — |
| | | | 10 | 46.0 | — |
| | | | 5 | 26.4 | — |
| SEQ ID NO: 5 | WEQEFLRR | acetyl | 100 | 81.6 | — |
| | | | 50 | 51.5 | — |
| | | | 10 | 52.8 | — |
| | | | 1 | 22.0 | — |
| | | | 0.1 | 19.0 | — |
| | | palmitoyl | 50 | 17.9 | — |
| | | | 10 | 24.7 | — |
| | | | 5 | 25.1 | — |
| | | | 1 | 16.1 | — |
| | | | 0.1 | 16.4 | — |

All peptides were functionally validated as inhibitors of regulated neuronal exocytosis on neuroblastoma cell line. In particular, acetylated form of SEQ ID NOS: 1, 2, 4 and 5 significantly diminished ACh release between 50-87% at a concentration of 10 μM as TFA salt, and around 40% as acetate salt at 0.1 μM. Palmitoylated SEQ ID NO: 4 significantly reduced acetylcholine release around 50% at 10 μM. The most potent peptide was palmitoylated SEQ ID NO: 3, as it was active at the lowest concentration tested 0.1 μM. Overall, all effective peptides were in the micromolar range.

Example 4: Cell Viability Assays on Human Epidermal Keratinocytes and Dermal Fibroblasts This example evaluated effects of the peptides of invention on human epidermal keratinocytes and dermal fibroblasts. Cell viability was determined with the 3-(4,5-dimethyl-2-thiazolyl)-2,5-diphenyl-2H-tetrazolium bromide (MTT) assay. The MTT assay is a colorimetric reaction based on the capacity of the mitochondrial dehydrogenase enzyme to break and transform the tetrazolium rings of MTT. Epidermal keratinocytes (HEKa) were seeded in a previously coated 96 well-plate at 50-60% confluence in 100 μL of supplemented corresponding medium. Dermal fibroblasts (HDFa) were seeded in a 96 well-plate at 70% confluence in 100 μL supplemented medium. For both cell lines, 24 hours after seeding, medium was replaced by fresh supplemented medium containing peptides dissolved at concentration range between 0.1 and 200 μM. All test substances were incubated for 24 hours at 37° C. and 5% $CO_2$. Afterwards, medium was replaced by 0.5 mg/ml of MTT solution for 4 hours in complete medium. Then, medium was carefully removed and 150 μL/well of DMSO were added to solubilize formazan crystals. Plate was protected from light, shaken for 60 seconds and optical density was measured at 570 nm with a reference filter of 620 nm. Table F details effects of peptides of invention on keratinocytes and fibroblasts cell viability expressed as percentage of inhibition.

TABLE F

| Peptide | Sequence | Nt Derivatization | µM | % inhibition cell viability | |
|---|---|---|---|---|---|
| | | | | HEKa | HDFa |
| SEQ ID NO: 1 | HYWRELQYR | acetyl (acetate salt) | 200 | 9.5 | 2.9 |
| | | | 100 | 6.2 | 6.8 |
| | | | 50 | 7.4 | 3.9 |
| | | | 10 | 1.7 | 33 |
| | | | 5 | 8.8 | 9.7 |
| | | | 1 | −1.4 | 0.2 |
| | | Palmitoyl (acetate salt) | 50 | 37.5 | 31.6 |
| | | | 10 | 31.0 | 29.2 |
| | | | 5 | 23.6 | 24.3 |
| | | | 1 | 8.8 | 12.2 |
| | | | 0.5 | 6.4 | 7.2 |
| | | | 0.1 | 2.9 | 0.3 |
| SEQ ID NO: 2 | MQVWLRMWIDYRAT | acetyl (acetate salt) | 200 | 1.2 | 24.6 |
| | | | 100 | −0.7 | 7.8 |
| | | | 50 | −4.6 | 1.4 |
| | | | 10 | −0.5 | 8.5 |
| | | | 5 | −1.8 | 12.3 |
| | | | 1 | −1.2 | 10.1 |
| | | palmitoyl (acetate salt) | 50 | 32.5 | 35.3 |
| | | | 10 | 36.5 | 47.1 |
| | | | 5 | 36.9 | 47.3 |
| | | | 1 | 25.6 | 45.8 |
| | | | 0.5 | 20.9 | 42.9 |
| | | | 0.1 | 12.1 | 30.8 |
| SEQ ID NO: 3 | RRVVLVNNIL | palmitoyl (acetate salt) | 50 | 24.8 | 24.3 |
| | | | 10 | 22.4 | 27.2 |
| | | | 5 | 9.9 | 25.7 |
| | | | 1 | 11.7 | 8.7 |
| | | | 0.5 | −0.9 | 15.5 |
| | | | 0.1 | −3.8 | 6.0 |
| SEQ ID NO: 4 | LRVQMVNMFL | acetyl (acetate salt) | 200 | 41.1 | 22.9 |
| | | | 100 | 31.6 | 41.5 |
| | | | 50 | 19.5 | 40.6 |
| | | | 10 | 6.0 | 37.1 |
| | | | 5 | 2.6 | 28.4 |
| | | | 1 | 13.6 | 14.5 |
| | | palmitoyl (TFA salt) | 50 | 34.2 | 37.7 |
| | | | 10 | 18.0 | 40.9 |
| | | | 5 | 7.0 | 42.6 |
| | | | 1 | −7.6 | 34.2 |
| | | | 0.5 | 1.0 | 26.9 |
| | | | 0.1 | −6.2 | 15.2 |
| SEQ ID NO: 5 | WEQEFLRR | acetyl (TFA salt) | 200 | 23.7 | 14.7 |
| | | | 100 | 10.4 | 15.0 |
| | | | 50 | 4.3 | 10.0 |
| | | | 10 | 4.2 | 12.1 |
| | | | 5 | 0.8 | 10.0 |
| | | | 1 | −5.7 | 9.3 |
| | | palmitoyl (TFA salt) | 50 | −24.3 | 18.0 |
| | | | 10 | −6.3 | 7.6 |
| | | | 5 | −5.5 | 10.3 |
| | | | 1 | −2.9 | −0.2 |

Peptides of SEQ ID NOS: 1, 2 and 5 with Nt-acetyl substitution did not modify cell viability in human epidermal keratinocytes and dermal fibroblast up to 200 µM. Acetylated and palmitoylated peptide with SEQ ID NO: 4 as did not modify keratinocyte viability when assessed below 50 µM. Palmoylated SEQ ID NO: 3 did not modify keratinocyte and fibroblast viability at 1 UM or below.

Example 5: Evaluation the Antiperspirant Effect on Acute Administration in a Mouse Model of Sweat Secretion This example evaluated acute effects of the peptide of invention SEQ ID NO: 1, palmitoylated form, in an in vivo sweating model induced by pilocarpine. This model was established using pilocarpine, a non-selective agonist of muscarinic receptors, in 11-weeks old C57BL6/Rcc male mice. Test compound is the peptide of the invention having the following sequence (SEQ ID NO: 1):

Palm-HYWRELQYR-NH$_2$

Test compound was injected intraplantar (i.pl.) on the right hind paw (10, 30 and 100 µg) 30 min before sweating stimulation. Vehicle was saline solution.

Sweating was monitored through amylase activity detection on skin surface using iodine/starch reaction. Dark sweating drops were quantified after 5 minutes induction counting number of drops per paw in each condition. Sample n=5-6 individuals per group. Data are expressed as mean±standard error of the mean (SEM). Raw data was normalized as percentage respect to non-injected stimulated individuals (Control, 100%) and saline-injected non-stimulated individuals (Vehicle, 0%). Statistical analysis was one-way ANOVA followed by Dunnett's post-hoc multiple comparison test comparing each condition with the corresponding control group, **p<0.0001 *p<0.001 **p<0.01, *p<0.05

The results are summarized in the following Table G.

TABLE G

| Palm-SEQ ID NO: 1 | % Inhibition | SEM | Statistic |
|---|---|---|---|
| 10 µg/paw | 58.2 | ±9.8 | *** |
| 30 µg/paw | 51.4 | ±9.6 | ** |
| 100 µg/paw | 34.5 | ±8.4 | * |

Test compound significantly reduced sweating at 10, 30 and 100 µg.

Example 6: Evaluation the Antiperspirant Effect on Chronic Administration in a Mouse Model of Sweat Secretion This example evaluated chronic effects of peptide of invention SEQ ID NO: 1 pamitoylated form, in an in vivo sweating model. This model was established using pilocarpine, a non-selective agonist of muscarinic receptors, in 11-weeks old C57BL6/Rcc male mice. Test compound was locally administered three times per week for 4 weeks (Treatment). Sweat was induced by intraplantar (i.pl) injection of pilocarpine (3 µg/paw) in the right hind paw (Sweating) once on weeks 1, 2 and 4 according to table H.

TABLE H

| Week | Monday | Tuesday | Wednesday | Thursday | Friday |
|---|---|---|---|---|---|
| 1 | Treatment | Sweating | Treatment | — | Treatment |
| 2 | Treatment | Sweating | Treatment | — | Treatment |
| 3 | Treatment | — | Treatment | — | Treatment |
| 4 | Treatment | Sweating | Treatment | — | Treatment |

Test compound is the peptide of the invention having the following sequence (SEQ ID NO: 1):

Palm-HYWRELQYR-NH$_2$

Test compound was injected i.pl. on the right hind paw (1, 10 and 100 µg), and vehicle was saline solution.

Sweating was monitored through amylase activity detection on skin surface using iodine/starch reaction. Dark sweating drops were quantified after 5 minutes induction counting number of drops per paw in each condition. Sample n=5-6 individuals per group. Data are expressed as mean ±standard error of the mean (SEM). Raw data was normalized as percentage respect to non-injected stimulated individuals (control, 100%). Statistical analysis was one-way ANOVA followed by Dunnett's post-hoc multiple comparison test comparing each condition with the corresponding control group, **p<0.0001 *p<0.001 **p<0.01, *p<0.05

Results are summarized in the following Table I.

TABLE I

|  | Palm-Seq ID No1 | % Inhibition | SEM | Statistic |
|---|---|---|---|---|
| Week 1 | 1 μg/paw | 2.6 | ±9.7 |  |
|  | 10 μg/paw | 11.2 | ±9.7 |  |
|  | 100 μg/paw | 24.2 | ±6.2 | ** |
| Week 2 | 1 μg/paw | 26.7 | ±6.7 |  |
|  | 10 μg/paw | 27.3 | ±5.4 |  |
|  | 100 μg/paw | 27.1 | ±5.0 | * |
| Week 4 | 1 μg/paw | −4.3 | ±11.9 |  |
|  | 10 μg/paw | 11.3 | ±3.6 |  |
|  | 100 μg/paw | 25.2 | ±3.2 | * |

Palm-SEQ ID NO: 1 showed significant sweating inhibition during 4 weeks treatment when tested at 100 μg/paw.

Example 7: In Vitro Functional Assay for Neuronal Sensitization

This example evaluated in vitro effects of palmitoylated form of SEQ ID NO: 1 in nociceptor sensitization in a sensitive skin context.

Isolated neonatal rat dorsal root ganglia from Wistar rats (3-5 days-old) were seeded microelectrode array chips in DMEM Glutamax, 10% FBS, 1% P/S supplemented with murine NGF. All experiments were performed after 48 h cell seeding.

Sensory neurons were sensitized by acute exposure to pro-inflammatory cocktail with bradykinin, histamine and ATP. TRPV1-mediated excitability was analyzed as stinging, burning and itching sensations are mainly driven by TRPV1. Repetitive application of TRPV1-agonist capsaicin (15 s-application 500 nM) allowed first activation (P1) followed by desensitization (second application). Desensitized cultures were sensitized with the cocktail to recover excitability, using external solution between the second (P2) and the third (P3) capsaicin pulse (8 min). To confirm cell viability 40 mM KCl was applied at the end. Test compound was incubated 1 hour before monitoring at 0.1, 1 and 10 UM. Test compound is the peptide having the following sequence (SEQ ID NO: 1):

Palm-HYWRELQYR-NH$_2$

Sensitization was calculated as ratio between P3 and P1 capsaicin pulse (ratio P3/P1), representing sensitized response induced by the pro-inflammatory cocktail. Inhibition percentage was calculated as 100-Sensitization. Data are expressed as mean±standard error of the mean (SEM), Statistical analysis was one-way ANOVA followed by Dunnett's post-hoc multiple comparison test comparing each condition with the corresponding sensitization control group, **p<0.0001 *p<0.001 **p<0.01, *p<0.05

The results are summarized in the following Table J.

TABLE J

| Palm-HYWRELQYR-NH$_2$ | % Sensitization inhibition | SEM | Statistic |
|---|---|---|---|
| 0.1 μM | 69.7 | 2.7 | **** |
| 1 μM | 51.2 | 4.7 | **** |
| 10 μM | 59.7 | 3.3 | **** |

Test compound at the three concentration significantly inhibited sensitization process with similar efficacy.

The invention claimed is:

1. A purified or synthesized peptide or a salt thereof, comprising the sequence of SEQ ID NO: 1:
wherein the peptide or the salt thereof is no more than 20 amino acids in length.

2. The peptide or the salt thereof according to claim 1 that is no longer than 15 amino acid residues.

3. The peptide or the salt thereof according to claim 1 that is no longer than 10 amino acid residues.

4. The peptide or the salt thereof according to claim 1, wherein the salt is selected from the group consisting of a salt of hydrochloric acid, acetic acid, trifluoroacetic acid, oxalic acid, maleic acid, methanesulfonic acid, para-toluenesulfonic acid, succinic acid, citric acid, tartaric acid, and lactic acid.

5. The peptide or the salt thereof according to claim 1, wherein the salt is at least one selected from the group consisting of a salt of a mono-, di- and tri-alkylamine, a mono-, di- and tri-alkanolamine, guanidine, morpholine, piperidine, pyrrolidine, piperazine, l-butylpiperidine, 1-ethyl-2-methyl-piperidine, N-methylpiperazine, 1,4-dimethylpiperazine, N-benzylphenylethylamine, N-methylglucosamine, and tris(hydroxymethyl)aminomethane.

6. A cosmetic composition comprising (D) the peptide or salt thereof according to claim 1 and (ii) at least one cosmetically acceptable ingredient.

7. A pharmaceutical composition comprising (i) the peptide or a salt thereof according to claim 1 and (ii) at least one pharmaceutically acceptable ingredient.

8. A method for inhibiting cholinergic calcitonin gene-related peptide (CGRP) release and acetylcholine (ACh) release or inhibiting sensitization-mediated by transient receptor potential vanilloid 1 (TRPV1) mediated excitability in sensory neurons in a subject in need thereof, comprising topical application to the subject a pharmaceutical or cosmetic composition comprising (i) the peptide or the salt thereof according to claim 1 and (ii) at least one pharmaceutically or cosmetically acceptable ingredient; wherein the subject suffers from skin conditions with hyper-perspiration mediated by cholinergic CGRP or hyperhidrosis mediated by cholinergic CGRP, or sensitive skin conditions mediated by TRPV1-medicated excitability in sensory neurons.

9. A method for inhibiting hyper-perspiration mediated by cholinergic CGRP or hyperhidrosis mediated by cholinergic CGRP release in a subject in need thereof, comprising administering to the subject the peptide or the salt thereof according to claim 1.

10. A purified or synthesized peptide variant or a salt thereof, wherein the peptide variant is the peptide that comprises the sequence of SEQ ID NO: 1 according to claim 1, and has an acetylated or palmitoylated N terminus, and wherein the peptide variant or the salt thereof is no more than 20 amino acid residues in length.

11. The peptide variant or the salt thereof according to claim 10, wherein the peptide variant or the salt thereof has an acetylated N terminus.

12. The peptide variant or the salt thereof according to claim 10, wherein the peptide variant or the salt thereof has a palmitoylated N terminus.

13. The peptide variant or the salt thereof according to claim 10 that is no longer than 15 amino acid residues.

14. The peptide variant or the salt thereof according to claim 10 that is no longer than 10 amino acid residues.

15. The peptide variant or the salt thereof according to claim 10, wherein the salt is selected from the group consisting of a salt of hydrochloric acid, acetic acid, trifluoroacetic acid, oxalic acid, maleic acid, methanesulfonic acid, para-toluenesulfonic acid, succinic acid, citric acid, tartaric acid, and lactic acid.

16. The peptide variant or the salt thereof according to claim 7, wherein the salt is at least one selected from the group consisting of a salt of mono-, di- and tri-alkylamine, a mono-, di- and tri-alkanolamine, guanidine, morpholine, piperidine, pyrrolidine, piperazine, 1-butylpiperidine, 1-ethyl-2-methyl-piperidine, N-methylpiperazine, 1,4-dimethylpiperazine, N-benzylphenylethylamine, N-methylglucosamine, and tris(hydroxymethyl)aminomethane.

17. A cosmetic composition comprising (i) the peptide variant or the salt thereof according to claim 10 and (ii) at least one cosmetically acceptable ingredient.

18. A pharmaceutical composition comprising (i) the peptide variant or the salt thereof according to claim 10 and (ii) at least one pharmaceutically acceptable ingredient.

19. A method for inhibiting cholinergic calcitonin gene-related peptide (CGRP) release and acetylcholine (ACh) release or inhibiting sensitization-mediated by TRPV1-mediated excitability in sensory neurons in a subject in need thereof comprising the topical application to the subject a pharmaceutical or cosmetic composition comprising (i) the peptide variant or the salt thereof according to claim 10 and (ii) at least one pharmaceutically or cosmetically acceptable ingredient; wherein the subject suffers from skin conditions with hyper-perspiration mediated by cholinergic CGRP or hyperhidrosis mediated by cholinergic CGRP, or sensitive skin conditions mediated by TRPV1-medicated excitability in sensory neurons.

20. A method for inhibiting hyper-perspiration mediated by cholinergic CGRP or hyperhidrosis mediated by cholinergic CGRP release in a subject in need thereof comprising administering to the subject the peptide variant or the salt thereof according to claim 10.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

His Tyr Trp Arg Glu Leu Gln Tyr Arg
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 2

Met Gln Val Trp Leu Arg Met Trp Ile Asp Tyr Arg Ala Thr
1               5                   10

<210> SEQ ID NO 3
<211> LENGTH: 10
<212> TYPE: PRT
<213> ORGANISM: Artificial Sequence

```
<220> FEATURE:
<223> OTHER INFORMATION: Synthetic Peptide

<400> SEQUENCE: 3

Arg Arg Val Val Leu Val Asn Asn Ile Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Leu Arg Val Gln Met Val Asn Met Phe Leu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Trp Glu Gln Glu Phe Leu Arg Arg
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Arg Lys Val Val Leu Val Asn Gln Ile Leu
1               5                   10
```